United States Patent
Wakayama

(10) Patent No.: US 9,594,001 B2
(45) Date of Patent: Mar. 14, 2017

(54) ULTRASONIC TESTING DEVICE AND ULTRASONIC TESTING METHOD

(71) Applicant: FUJI JUKOGYO KABUSHIKI KAISHA, Tokyo (JP)

(72) Inventor: Hiroshi Wakayama, Tokyo (JP)

(73) Assignee: FUJI JUKOGYO KABUSHIKI KAISHA, Tokyo (JP)

( * ) Notice: Subject to any disclaimer, the term of this patent is extended or adjusted under 35 U.S.C. 154(b) by 71 days.

(21) Appl. No.: 14/850,161

(22) Filed: Sep. 10, 2015

(65) Prior Publication Data

US 2016/0084730 A1    Mar. 24, 2016

(30) Foreign Application Priority Data

Sep. 22, 2014  (JP) ................................. 2014-192278

(51) Int. Cl.
  *G01N 29/28*  (2006.01)
  *G01N 29/265*  (2006.01)
  (Continued)

(52) U.S. Cl.
  CPC ............ *G01M 3/24* (2013.01); *G01M 3/2884* (2013.01); *G01M 3/3272* (2013.01); *G01N 29/04* (2013.01);
  (Continued)

(58) Field of Classification Search
  CPC .... F16H 2048/385; G01H 1/00; G01H 3/125; G01N 29/0681; G01N 29/28;
  (Continued)

(56) References Cited

U.S. PATENT DOCUMENTS 4,297,885 A * 11/1981 Hein, Jr. .................. G01H 1/00
                                                              73/587
4,866,986 A *  9/1989 Cichanski .............. G01H 3/125
                                                              73/600
(Continued)

FOREIGN PATENT DOCUMENTS

JP             06167479 A  *  6/1994
JP         2001-201485         7/2001
(Continued)

OTHER PUBLICATIONS

Decision to Grant Patent mailed Sep. 27, 2016 relative to JP2014-192278 (with English Translation) 6 pages.
(Continued)

*Primary Examiner* — David A Rogers
(74) *Attorney, Agent, or Firm* — Smith, Gambrell & Russell, LLP

(57) ABSTRACT

An ultrasonic testing device includes: a liquid tank that stores the liquid into which the differential casing is to be immersed; a workpiece holder that holds the differential casing and immerses the differential casing into the liquid in the liquid tank; an ultrasonic probe that conducts an ultrasonic testing of the welded part of the differential casing by irradiating the ultrasonic wave to the welded part and receiving a reflected wave; an image processing module that generates an ultrasonic image based on the reflected wave received by the ultrasonic probe; and a replacer that replaces gas inside an air gap formed at a weld toe of the welded part with test liquid. The replacer replaces the gas inside the air gap by the test liquid before the ultrasonic probe irradiates the ultrasonic wave.

16 Claims, 4 Drawing Sheets

(51) Int. Cl.
*G01N 29/27* (2006.01)
*G01M 3/24* (2006.01)
*G01N 29/04* (2006.01)
*G01M 3/28* (2006.01)
*G01M 3/32* (2006.01)

(52) U.S. Cl.
CPC .......... *G01N 29/043* (2013.01); *G01N 29/28* (2013.01); *G01N 2291/044* (2013.01); *G01N 2291/267* (2013.01)

(58) Field of Classification Search
CPC .......... G01N 29/265; G01N 2223/646; G01N 2291/044; G01N 2291/2675; G01N 23/203; G01N 29/14
See application file for complete search history.

(56) References Cited

U.S. PATENT DOCUMENTS

| | | | | |
|---|---|---|---|---|
| 6,378,761 B2* | 4/2002 | Eulenstein | ............. | B23K 20/16 228/246 |
| 6,656,079 B2* | 12/2003 | Eulenstein | ............. | F16H 48/08 475/230 |
| 6,981,417 B1* | 1/2006 | Oravecz | ............. | G01N 29/0609 73/612 |
| 8,855,268 B1* | 10/2014 | Safai | ............. | G01N 23/203 378/130 |
| 8,876,649 B2 | 11/2014 | Uchida et al. | | |
| 9,170,236 B2* | 10/2015 | Kessler | ............. | G01N 29/0681 |
| 2004/0173024 A1* | 9/2004 | McKeon | ............. | G01N 29/0681 73/644 |
| 2007/0029290 A1* | 2/2007 | Kehrer | .................. | B23K 26/28 219/121.14 |
| 2012/0125110 A1* | 5/2012 | Kessler | ............. | G01N 29/0681 73/606 |
| 2013/0195545 A1* | 8/2013 | Tsuchida | ................ | F16H 48/40 403/270 |
| 2014/0083191 A1* | 3/2014 | Iwatani | ................ | G01N 29/043 73/588 |
| 2014/0318250 A1 | 10/2014 | Arai et al. | | |
| 2016/0041128 A1* | 2/2016 | Kessler | ............. | G01N 29/0681 73/621 |

FOREIGN PATENT DOCUMENTS

| | | |
|---|---|---|
| JP | 2001289826 A * | 10/2001 |
| JP | 2011-169444 | 9/2010 |
| WO | 2011-158330 A1 | 12/2011 |
| WO | 2013-018223 A1 | 3/2015 |
| WO | 2013-076850 A1 | 5/2015 |

OTHER PUBLICATIONS

Japanese Office Action mailed Mar. 1, 2016 relative to JP2014-192278 (with English Translation) 5 pages.

* cited by examiner

ULTRASONIC TESTING DEVICE AND ULTRASONIC TESTING METHOD

CROSS-REFERENCE TO RELATED APPLICATION

The present application claims priority from Japanese Patent Application No. 2014-192278 filed on Sep. 22, 2014, the entire contents of which are hereby incorporated by reference.

BACKGROUND

1. Technical Field

The present disclosure relates to an ultrasonic testing device and an ultrasonic testing method by which a workpiece (or an object) is tested using ultrasonic waves, and particularly to art effective in blowhole detection of a workpiece that normally have an air gap at a weld toe.

2. Related Art

Casings of differentials (i.e., differential casings) provided as final drive units used for vehicles, such as automobiles, have a structure in which, for example, a ring gear of a hypoid gear set is joined to the outer circumference of the differential casing.

The ring gear is joined to the differential casing by welding, and a welding technique, such as laser welding, is widely used for this purpose. Laser welding is a joining technique to irradiate a laser beam to a joining part between the differential casing and the ring gear, thus the joining part is molten and then solidified.

Inspections (or tests) of the weld quality is then conducted, for example, by using an ultrasonic testing device for each piece of the differential casing onto which the ring gear is welded. The ultrasonic testing device is as device that detects a blowhole, i.e., a minute defect that is comprised of a spherical or almost spherical hollow part caused in deposited metal.

Ultrasonic testing is a technique to test (or evaluate) a defect based on an ultrasonic wave reflected back from the defect. The differential casing onto which the ring gear is welded is first immersed into liquid filled in a liquid tank. An ultrasonic wave is then transmitted from an ultrasonic probe that is similarly immersed in the liquid of the liquid tank, and the ultrasonic wave reflected on the defect is received by the probe for the evaluation. The differential casing and the ultrasonic probe are immersed into the liquid in order to prevent the ultrasonic wave from being reflected on air layer.

For example, Japanese Unexamined Patent Application Publication (JP-A) No. 2001-201485 addresses an improvement in accuracy of the evaluation for the type of ultrasonic testing technique with the workpiece immersed. Specifically, when the workpiece is immersed into liquid (water) of a liquid tank, a large temperature difference between the workpiece and water where the workpiece is immersed is prevented to be caused, and thereby improving the accuracy.

SUMMARY OF THE INVENTION

When welding the ring gear to the differential casing, the welding is conducted along the outer circumference of the part where the ring gear contacts the differential casing in a state where the ring gear is fitted onto the differential casing. In such a case, an air gap is inevitably formed at a weld toe of the differential casing and the ring gear, and welding is not conducted in the air gap created inside the differential casing.

If the air gap exists, when the ultrasonic wave is transmitted toward the welding area in order to conduct the ultrasonic testing, the transmitted ultrasonic wave is reflected on the air gap, and thereby the reflection of the ultrasonic wave on the air gap may be detected as the defect due to blowhole. As the result, the detection accuracy of the weld defect is deteriorated.

It is desirable to provide a technique with an improved detection accuracy in defect inspection of welding for a workpiece having an air gap, for example, at a weld toe.

An aspect of the present disclosure provides an ultrasonic testing device that immerses a differential casing to which a ring gear is welded into liquid, and detects a weld defect in a welded part of the differential casing based on an ultrasonic wave. The device includes a liquid tank that stores the liquid into which the differential casing is to be immersed, a workpiece holder that holds the differential casing and immerses the differential casing into the liquid in the liquid tank, an ultrasonic probe that conducts an ultrasonic testing of the welded part of the differential casing by irradiating the ultrasonic wave to the welded part and receiving a reflected wave, an image processing module that generates an ultrasonic image based on the reflected wave received by the ultrasonic probe, and a replacer that replaces gas inside an air gap formed at a weld toe of the welded part with test liquid. The replacer replaces the gas inside the air gap with the test liquid before the ultrasonic probe irradiates the ultrasonic wave.

Another aspect of the present disclosure provides an ultrasonic testing method that tests a workpiece with an ultrasonic wave. The method includes immersing a differential casing to which a ring gear is welded into liquid stored in a liquid tank, and detecting a weld defect in a welded part of the differential casing with an ultrasonicwave. The method also includes immersing the differential casing into the liquid, replacing gas inside an air gap formed at a weld toe of the welded part with test liquid, and conducting the detection of the weld defect by the ultrasonic wave after the gas inside the air gap is replaced.

BRIEF DESCRIPTION OF THE DRAWINGS

The present disclosure is illustrated by way of example and not by way of limitation in the figures of the accompanying drawings, in which the like reference numerals indicate like elements and in which.

DETAILED DESCRIPTION

Figure 1:
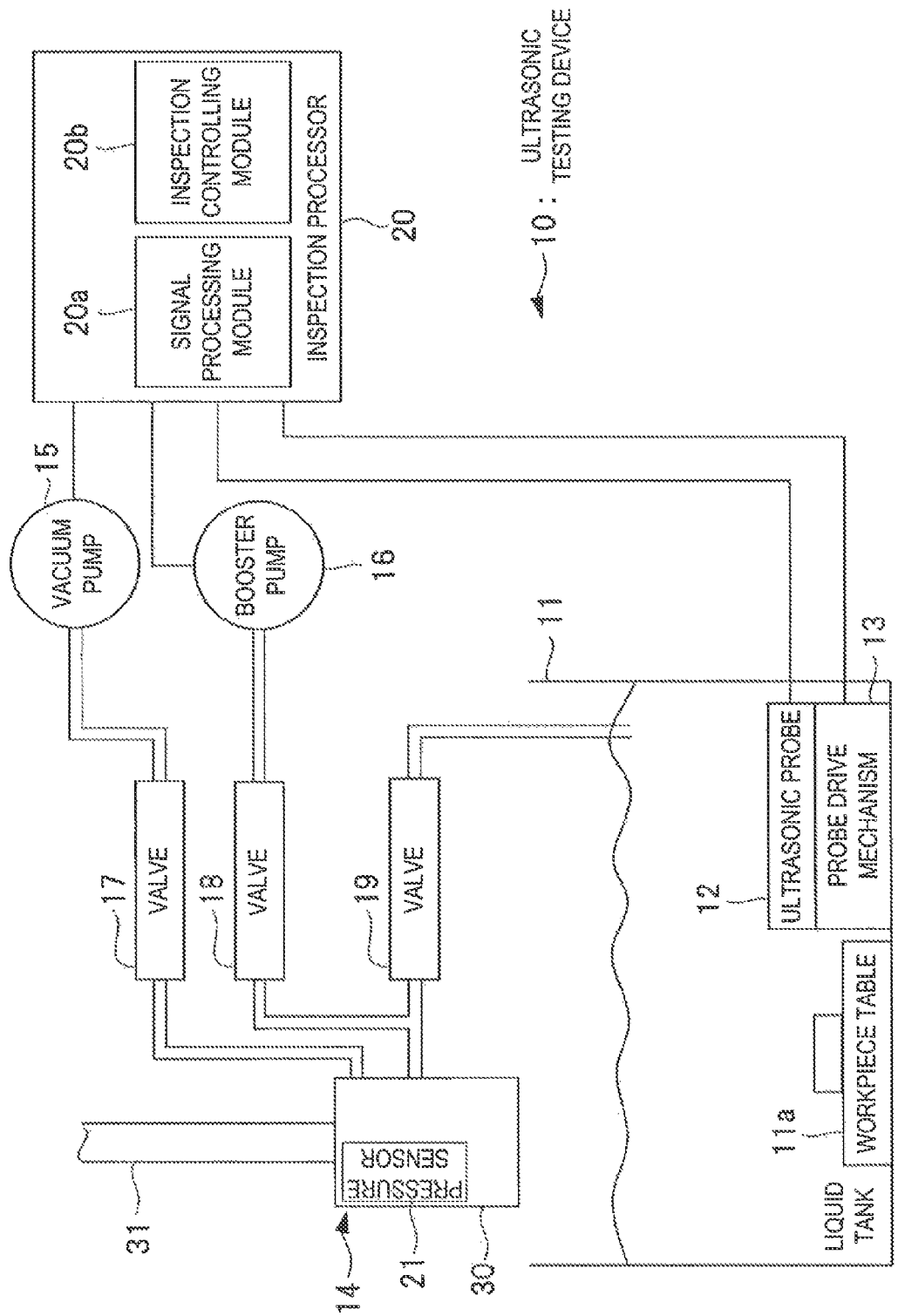
FIG. 1 illustrates an example configuration of an ultrasonic testing device according to an implementation of the present invention.

In the following implementation of the present disclosure, if necessary for convenience, this detailed description may be described while divided into a plurality of sections or examples. However, unless otherwise explicitly described, these sections or examples may be mutually related, thus one of the sections or examples may have relations of modifications, details, and/or supplementary explanations of all or part of others.

In the following implementation, when referring to values related to components or elements (i.e., numbers, numerical values, amounts or quantities, ranges, etc. of components or elements), the values should not be limited to particular values, unless otherwise explicitly described or theoretically limited to the particular values. Therefore, the values may be more or less than the particular values.

In the following implementation, the components or elements (including steps of processing or method) are not essential to the configuration of this disclosure, unless otherwise explicitly described or theoretically essential to the configuration of this disclosure.

Similarly, in the following implementation, when referring to geometries of the components or elements, the geometries may include substantially approximated or similar shapes, unless otherwise explicitly described or theoretically thought to have other geometries. This can also be said for the values and ranges described above.

Like reference numerals or characters are fundamentally used for like components or elements throughout the accompanying drawings illustrating the implementation in order to omit redundant explanations. Note that, in the drawings, hatching may be drawn in views other than cross-sectional views for convenience of easier understandings.

Hereinafter, the implementation is described in detail with reference to the accompanying drawings.

Configuration of Ultrasonic Testing Device

Figure 2:
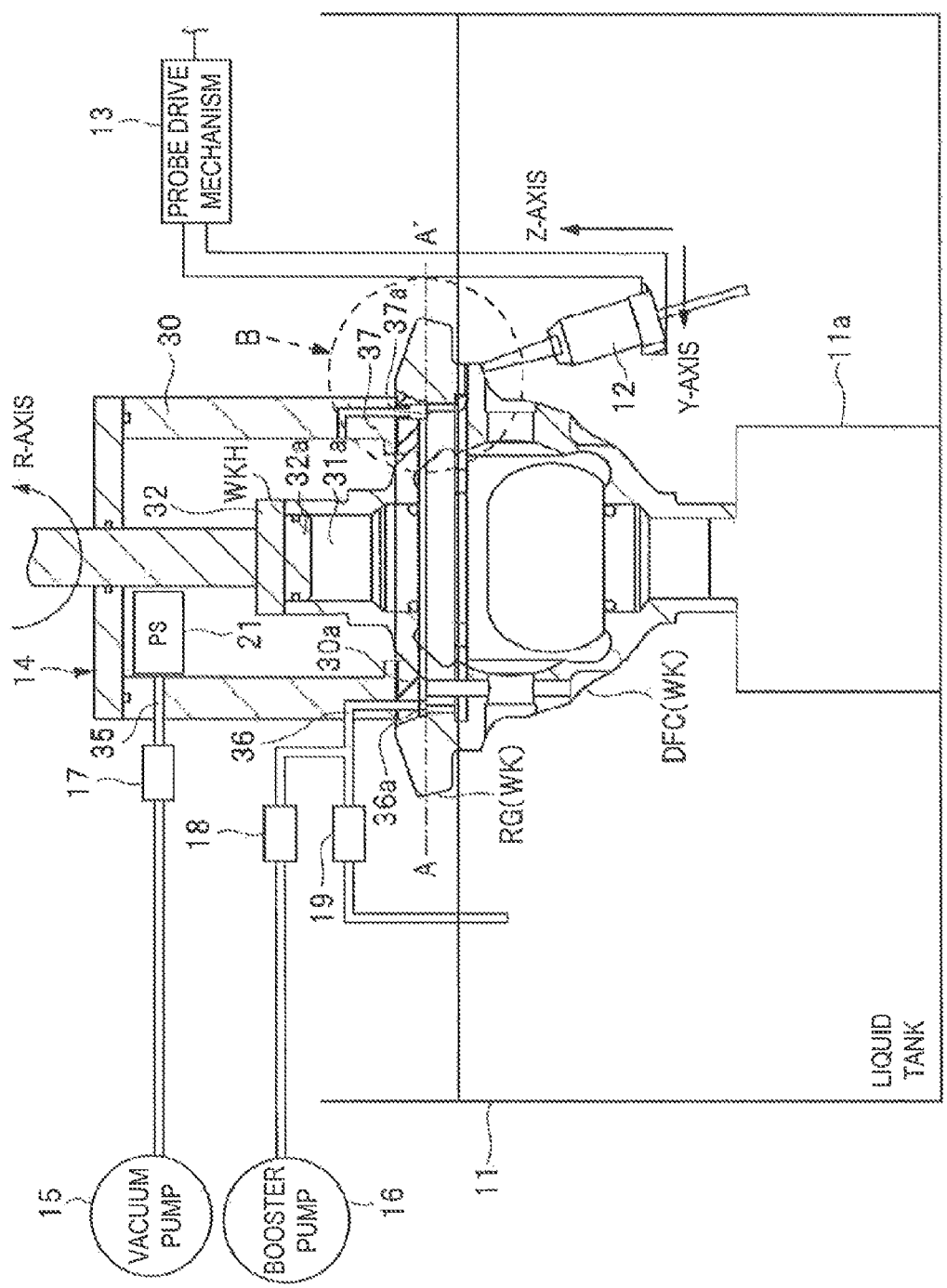
FIG. 2 is illustrates one example in the case of a welding inspection of a workpiece by the ultrasonic testing device of FIG. 1.
Figure 3:
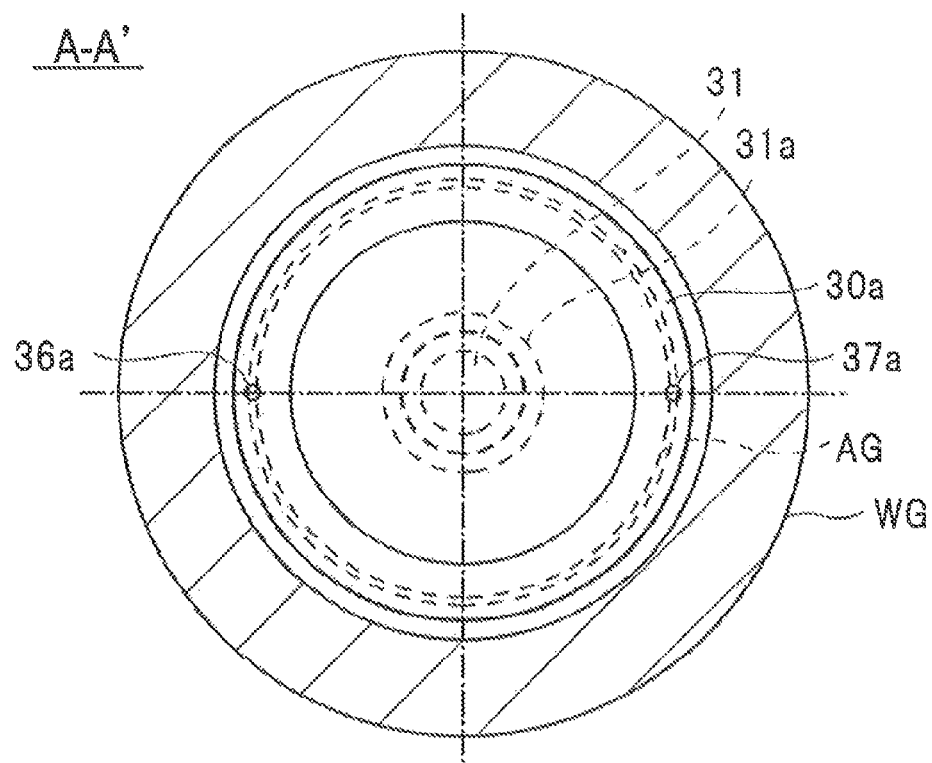
FIG. 3 is a cross-sectional view taken along a line A-A' of FIG. 2.

FIG. 1 illustrates an example configuration of an ultrasonic testing device 10 according to the implementation of the present invention. FIG. 2 illustrates one example in the case of a welding inspection of a workpiece by the ultrasonic testing device 10 of FIG. 1. FIG. 3 is a cross-sectional view taken along a line A-A' of FIG. 2. Note that FIG. 2 illustrates a workpiece WK immersed in liquid of a liquid tank 11, a rotary holder jig 14, and the valves 17 to 19, and the workpiece WK and the rotary holder jig 14 are illustrated in cross section.

The ultrasonic testing device 10 is a device that inspects a weld defect of the workpiece WK. The workpiece WK is a differential casing DFC to which a ring gear RG of a hypoid gear set is welded by, for example but not limited to laser welding.

As illustrated in FIGS. 1 to 3, the ultrasonic testing device 10 includes the liquid tank 11, an ultrasonic probe 12, a probe drive mechanism 13, the rotary holder jig 14, a vacuum pump 15, a booster pump 16, the valves 17 to 19, an inspection processor 20, and a pressure sensor (PS) 21.

The liquid tank 11 is a bathtub-like tank where a sufficient amount of liquid for immersing the workpiece WK therein is reserved. The liquid may be, for example but not limited to, alkaline water or oil having a pH of about 10 (hereinafter, the liquid may be referred to as "test liquid"). The ultrasonic probe 12 is disposed inside the liquid tank 11. The ultrasonic probe 12 is disposed so as to be immersed in the liquid of the liquid tank 11 together with the workpiece WK when an ultrasonic testing of the workpiece WK is conducted. The ultrasonic probe 12 is what is called a sounding probe that oscillates and transmits an ultrasonic wave toward the workpiece WK and receives a reflected wave from the workpiece WK.

The reflected wave received by the ultrasonic probe 12 is outputted to the inspection processor 20. The inspection processor 20 has a signal processing module 20a and an inspection controlling module 20b. In one implementation, the signal processing module 20a may serve as an "image processing module". The signal processing module 20a generates an ultrasonic image based on, for example but not limited to, the reflected wave received by the ultrasonic probe 12 in order to determine the existence of poor welding.

The probe drive mechanism 13 drives the ultrasonic probe 12. This probe drive mechanism 13 is provided with, for example but not limited to, an offset mechanism and a focal mechanism to drive the ultrasonic probe 12 based on a driving control signal outputted from the inspection controlling module 20b. In one implementation, the inspection controlling module 20b may serve as a "determination module".

The offset mechanism moves the ultrasonic probe 12 in parallel to the surface of liquid (i.e., horizontal direction). This direction is herein referred to as a Y-axis direction, as illustrated in FIG. 2. A measurement pitch of the ultrasonic probe 12 is determined by the offset mechanism. Higher precision of the measurement can be achieved by setting the measurement pitch smaller.

The focal mechanism moves the ultrasonic probe 12 perpendicular to the surface of liquid (i.e., vertical). This direction is herein referred to as a Z-axis direction, as illustrated in FIG. 2. The focal mechanism moves the ultrasonic probe 12 so that a focal distance between the ultrasonic probe 12 and the inspecting part of the workpiece WK is kept substantially.

A workpiece table 11a is provided at the bottom of the liquid tank 11. The workpiece table 11a is a stage where the workpiece WK is placed, and is rotatable while the workpiece WK is placed thereon. The rotary holder jig 14 is provided above the liquid tank 11. In one implementation, the rotary holder jig 14 may serve as a "workpiece holder".

The vacuum pump 15 is a pump that creates a vacuum. The booster pump 16 may be, for example but not limited to, an air compressor that discharges compressed air. The valves 17 to 19 may be, for example but not limited to, solenoid valves that adjust a flow volume based on control signals from the inspection controlling module 20b.

Example Connections of Rotary Holder Jig and Valves

Here, connections of the rotary holder jig 14, the vacuum pump 15, the booster pump 16, and the valves 17 to 19 are described with reference to FIG. 2.

The rotary holder jig 14 is a jig that fixes or holds the workpiece WK placed on the workpiece table 11a, and rotates the workpiece WK while the workpiece WK is inspected for a weld defect thereof. The rotary holder jig 14 has a dome part 30. The dome part 30 may be a vertical cylinder that is covered at the top end.

The pressure sensor 21 is provided to the dome part 30. The pressure sensor 21 measures an internal pressure of the dome part 30, and a result of measurement of the pressure sensor 21 is outputted to the inspection controlling module 20b.

An annular seal rubber 30a is provided at the bottom end of the dome part 30 to seal the inside of the dome part 30 by closely contacting with the workpiece WK. A driving rod 31, which may be a circular bar, is provided to the dome part 30 so as to penetrate the top end of the dome part 30.

A jig actuator, such as, but not limited to, a motor (not illustrated), is connected with the upper end of the driving rod 31 located above the dome part 30. The workpiece WK placed on the workpiece table 11*a* is rotated by operating the jig actuator.

A workpiece holding part 32 that fixes or holds the workpiece WK is provided at the lower end of the driving rod 31 located inside the dome part 30. A holder shaft 32*a* is provided to the workpiece holding part 32 to be inserted into a center bore WKH of the workpiece WK. The workpiece WK is fixed in position by inserting the holder shaft 32*a* into the center bore WKH of the workpiece WK.

The rotary holder jig 14 can be moved by the jig actuator, from a loading station (not illustrated) to the liquid tank 11, and from the liquid tank 11 to an unloading station (not illustrated). The loading station is an area where the workpiece WK is placed when the workpiece WK is carried in from a previous process, such as a welding process, and the unloading station is an area from which the workpiece WK is removed for a next process after the ultrasonic testing is finished and where liquid adhered to the workpiece WK is removed after the ultrasonic testing.

A channel 35 is formed in the dome part 30. Channels 36 and 37 are also formed in the dome part 30 and the seal rubber 30*a*, respectively. The channel 35 is a hole penetrating the dome part 30 from the inner surface to the outer surface of the dome part 30, and the channel 35 is connected to one of connections of the valve 17. The other connection of the valve 17 is connected to the vacuum pump 15.

The channel 36 is a hole formed so as to penetrate the dome part 30 from the outer surface of the dome part 30 to the seal rubber 30*a* provided at the bottom end of the dome part 30. The channel 37 is a hole formed so as to penetrate the dome part 30 from the inner surface of the dome part 30 to the seal rubber 30*a*.

An opening 36*a* of the channel 36 is formed in the contacting surface of the seal rubber 30*a* with the workpiece WK, and an opening 37*a* of the channel 37 is similarly formed in the contacting surface of the seal rubber 30*a*. The opening 36*a* and the opening 37*a* are formed at positions opposing to air holes AR that are formed in the workpiece WK, respectively.

The air hole AH allows air heated and expanded by welding to escape. That is, releasing the heated air from the air hole AH during the welding prevents a poor weld of the ring gear RG which is the workpiece WK to the differential casing DFC.

In this implementation, the air hole AH is formed in the ring gear RG, and, more specifically, formed at two opposite positions on the circumference of the ring gear RG, the positions being separated from each other by 180 degrees on the circumference of the ring gear RG. Note that the air holes AH may be formed in at least one of the ring gear RG and the differential casing DFC.

The channel 36 is connected to one of connections of the valve 18 and one of connections of the valve 19. The other connection of the valve 19 is configured to be immersed in the test liquid. The other connection of the valve 18 is connected to the booster pump 16.

The inspection controlling module 20*b* controls operations of the jig actuator connected to the driving rod 31, the probe drive mechanism 13, the valves 17 to 19, the vacuum pump 15, and the booster pump 16.

In one implantation, a "replacer" may be comprised of the inspection controlling module 20*b*, the valves 17 to 19, the vacuum pump 15, and the booster pump 16.

Figure 4:
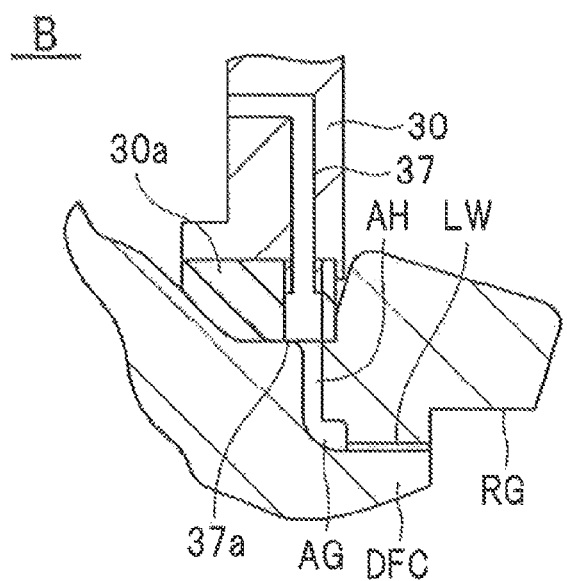
FIG. 4 is an enlarged view of a section B of FIG. 2.

FIG. 4 is an enlarged view of a section B of FIG. 2.

As illustrated in FIG. 4, laser welding LW is conducted along the outer circumference of the contacting part between the ring gear RG and the differential casing DFC onto which the ring gear RG is press-fitted.

An air gap AG where the welding is not conducted is created inside the differential casing DFC, at a weld toe of the differential casing DFC and the ring gear RG. The air gap AG communicates with the air holes AH, and the air holes AH communicate with the channel 37.

Example Operation of Ultrasonic Testing Device

Next, an inspection technique of the weld defect of the workpiece WK by the ultrasonic testing device 10 is described with reference to FIGS. 1 to 5.

Figure 5:
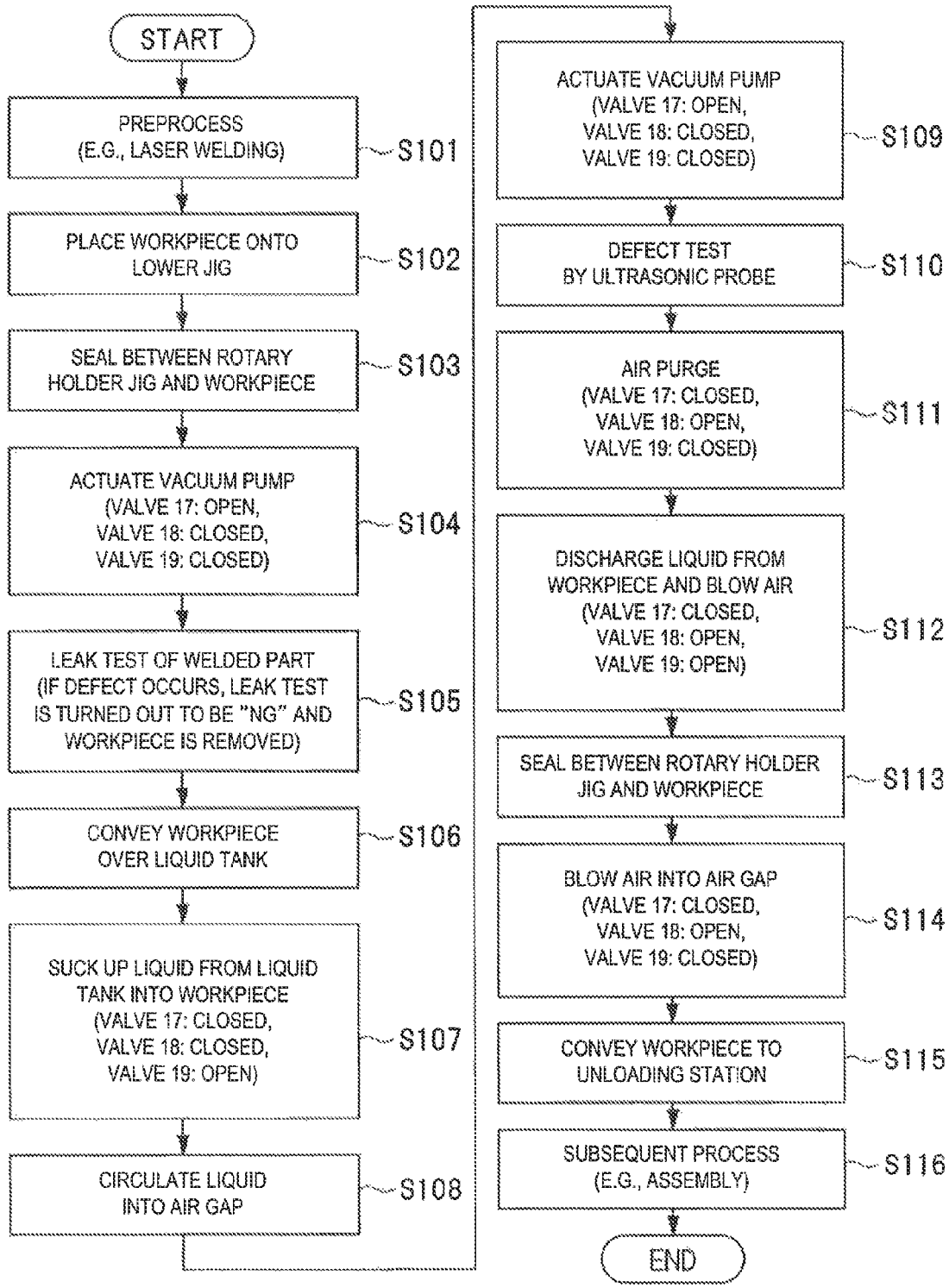
FIG. 5 is a flowchart illustrating one example of processing of an inspection of weld defect by the ultrasonic testing device of FIG. 1.

FIG. 5 is a flowchart illustrating one example of processing of an inspection of the weld defect by the ultrasonic testing device 10 of FIG. 1.

First, laser welding of the workpiece WK is conducted as a preprocess (step S101). At step S101, the laser welding of the differential casing DFC onto which the ring gear RG is press-fitted is conducted. The the ring gear RG is one example of the workpiece WK in this implementation.

The laser-welded workpiece WK is carried into the loading station (not illustrated) by a conveying mechanism (not illustrated). A lower jig where the workpiece WK is placed is formed in the loading station. The workpiece WK is placed onto the lower jig after the workpiece WK is aligned (step S102).

In the alignment processing, which is executed at step S103 described in detail later, the two air holes AH formed in the workpiece WK are aligned with the corresponding openings 36*a* and 37*a* of the rotary holder jig 14 when the workpiece WK is mounted to the rotary holder jig 14.

Then, the inspection controlling module 20*b* conducts sealing between the workpiece WK and the rotary holder jig 14 (step S103). At this step, the rotary holder jig 14 is lowered after the rotary holder jig 14 is moved above the workpiece WK by the jig actuator.

As the rotary holder jig 14 is lowered, the seal rubber 30*a* provided circumferentially in the bottom end of the dome part 30 closely contacts the workpiece WK, thus the press-fitted part of the ring gear RG onto the differential casing DFC is sealed. In addition, since the alignment processing is conducted at step S102, the two air holes AH formed in the workpiece WK are aligned with the openings 36*a* and 37*a*, respectively, so that the air holes AH become communicatable with the openings 36*a* and 37*a*.

Subsequently, the inspection controlling module 20*b* opens the valve 17, closes the valves 18 and 19, and actuates the vacuum pump 15 (step S104). Accordingly, a vacuum is created inside the dome part 30.

The inspection controlling module 20*b* stops the vacuum pump 15, closes the valve 17, and runs a leak test (step S105). Even if the air holes AH are formed in the workpiece WK, air may be heated and expanded during the welding and may create pores in the weld due to the heated and expanded air. Thus, the leak test inspects the existence of such defective pores caused during the welding.

If the defect, such as a pore, occurs in the weld, air leaks from the defect part and then enters into the dome part 30 from a gap of the press-fit between the differential casing DFC and the ring gear RG via a passage from the air hole AH to the opening 37*a*. Accordingly, the pressure inside the dome part 30 is dropped. Therefore, the inspection controlling module 20*b* monitors measurements of the pressure sensor 21 for a predetermined period of time, and determines whether there is any change in the pressure value. If the pressure value is changed during the monitoring period, the inspection controlling module 20b concludes that the leak test is turned out to be "poor (NG)."

By the leak test, the failed workpiece WK with pore(s) in the weld can be found before conducting a test of the ultrasonic testing device 10. Therefore, the total inspection cost and time can be reduced. Note that the leak test may be conducted by introducing compressed air into the dome part 30 from the booster pump 16 and monitoring a pressure change inside the dome part 30 by the pressure sensor 21 to determine the existence of the welding defects.

If "no leak" is determined, the inspection controlling module 20b again opens the valve 17 and actuates the vacuum pump 15 to create a vacuum inside the dome part 30. The inspection controlling module 20b causes the jig actuator to drive the rotary holder jig 14 so that the workpiece WK adsorbed to the rotary holder jig 14 by the vacuum is conveyed over the liquid tank 11 (step S106), and then causes the jig actuator to place the workpiece WK on the workpiece table 11a so that the workpiece WK is immersed into the test liquid in the liquid tank 11.

Thus, since the workpiece WK adsorbed to the rotary holder jig 14 by the vacuum can be moved after the leak test as it is, a dedicated conveying mechanism for the workpiece WK is not necessary to be provided. Therefore, components and cost of the ultrasonic testing device 10 can be reduced.

The inspection controlling module 20b stops the vacuum pump 15, closes the valve 17, and opens the valve 19 to suck up the test liquid from the liquid tank 11 (step S107), and fills up the air gap AG with the liquid as inspection liquid (step S108). Here, the valve 18 is closed.

As described above, the other connection of the valve 19 is immersed in the test liquid in the liquid tank 11. Here, since the inside of the dome part 30 is negative in pressure, the air gap AG connected to the channel 37 illustrated in FIG. 2 is also negative in pressure. Thus, when the valve 19 is opened, the test liquid in the liquid tank 11 flows into the channel 36 via the valve 19, and then flows into the air gap AG from the channel 36. Then, as soon as the air gap AG is filled by the liquid, the liquid flows out from the air holes AH via the channel 37 and into the dome part 30 so that the liquid is collected inside the dome part 30. Thus, gas inside the air gap AG is replaced by the test liquid. As described above, when replacing the gas inside the air gap AG by the test liquid, the preformed air holes AH in the workpiece WK is used. Therefore, a drilling or hole forming process is not necessary at this stage of inspection for the test liquid replacement. Since the drilling or hole forming process is not necessary, entry of foreign matters into the test liquid replacement system can be reduced, thus total labor and cost can also be reduced.

The supply of the test liquid into the air gap AG is conducted for a predetermined period of time. Thus, the air gap AG can be filled up with the test liquid. The predetermined period of time may be selected longer than the time needed for filling up the air gap AG, and preferably long enough to circulate the test liquid through the system so that Since the test liquid is supplied for the predetermined period of time such that be test liquid is the circulated in the air gap, flushing can be conducted in the air gap AG with the test liquid. Therefore, since the test liquid is circulated while filling up the air gap AG, debris caused from the laser welding and left in the system, such as the air gap AG or the weld toe (i.e., spatters) can be removed.

If the flushing is not conducted, the spatters separated from the workpiece WK would stick on teeth of a product differential to cause a gear bite or jam. However, if the spatters are removed by the flushing, reliability of the product can be improved.

Then, the inspection controlling module 20b opens the valve 17, closes the valves 18 and 19, and actuates the vacuum pump 15 to create a vacuum so that the negative pressure inside the dome part 30 is increased (step S109).

The adsorbing force of the workpiece WK is increased by increasing the negative pressure inside the dome part 30, and the inspection controlling module 20b then conducts an ultrasonic testing while operating the jig actuator to rotate the driving rod 31 about the center axis of the driving rod 31 (an R-axis direction indicated in FIG. 2) (step S110).

In this step, the ultrasonic probe 12 irradiates ultrasonic waves to the weld in the outer circumference of the workpiece WK and receives reflected waves, while rotating the driving rod 31 one turn in the R-axis direction. Then, the offset adjustment and the focal adjustment are conducted, and the weld of the workpiece WK is inspected, while rotating the driving rod 31 another turn in the R-axis direction.

In the offset adjustment, the offset mechanism moves the ultrasonic probe 12 only by a certain interval in the Y-axis direction illustrated in FIG. 2. In the focal adjustment, the focal mechanism moves the ultrasonic probe 12 in the Z-axis direction illustrated in FIG. 2 to adjust the focal distance to be substantially constant.

By repeating these processes, the ultrasonic probe 12 receives the reflected waves. The reflected waves received are outputted to the signal processing module 20a, and the signal processing module 20a generates an ultrasonic image from which the weld defect(s) are determined. Thus, the ultrasonic testing of the weld in the outer circumference of the workpiece WK is conducted.

In this implementation, the workpiece WK is rotated during the ultrasonic testing. Alternatively, the ultrasonic probe 12 may be rotated by additionally providing a rotating mechanism that rotates the ultrasonic probe 12 along the welded outer circumference of the workpiece WK.

Ultrasonic waves present a relatively good transmittance when entering into steel from liquid, such as water. However, when it enters into steel from air, the reflection factor becomes very large (e.g., about 100%). For this reason, when the air gap AG exists near the welded part, the air gap AG may be erroneously detected as a blowhole although there is actually no defect in the welded part.

The ultrasonic testing device 10 can reduce the reflection factor of the ultrasonic wave by filling up the air gap AG with the test liquid. Thus even if the air gap AG exists in, for example, the weld toe, it becomes possible to reduce the erroneous determination of the air gap AG as the blowhole, thereby achieving a high-precision defect inspection.

After the ultrasonic testing is finished, the inspection controlling module 20b conducts an air purge (step S111). In this air purge, the jig actuator is operated to move the rotary holder jig 14, to which the workpiece WK is adsorbed, to the unloading station. A lower jig (not illustrated) is provided at the unloading station, and the workpiece WK is placed on the lower jig.

When the workpiece WK is placed on the lower jig, the inspection controlling module 20b closes the valves 17 and 19, and opens the valve 18 to conduct the air purge of the inside of the dome part 30. That is, the inside of the dome part 30 is released to atmosphere.

The inspection controlling module 20b then operates the jig actuator to move the rotary holder jig 14 upward, and opens the closed valve 19.

Accordingly, the test liquid collected inside the dome part 30 is discharged. In addition, since the valves 18 and 19 are opened, compressed air and the like is discharged from the booster pump 16. As described above, the air blow inside the valves 18 and 19 and the channels thereof is conducted to remove the test liquid which remains inside the valves 18 and 19 and the channels thereof (step S112).

The inspection controlling module 20b then operates the jig actuator to lower the rotary holder jig 14, and again closely contacts the workpiece WK with the seal rubber 30a provided circumferentially in bottom end of the dome part 30 to seal therebetween (step S113).

When the sealing is finished, the inspection controlling module 20b closes the valves 17 and 19, and opens the valve 18 to conduct an air blow (step S114). By opening the valve 18, the compressed air and the like discharged from the booster pump 16 is discharged from the channel 36, fills up the air hole AH and the air gap AG, and is then discharged from the channel 37.

The test liquid adhered to corresponding parts, such as the air gap AG and the press-fitted part of the workpiece WK, can be removed by conducting the air blow using pressure, such as the compressed air discharged from the booster pump 16. Therefore, it can be prevented that the test liquid deposited on the workpiece WK may be mixed with transmission oil and/or differential oil, for example, in an assembly process.

Thereby, the inspection of the ultrasonic testing is finished. The inspected workpiece WK is then conveyed to the unloading station where the workpiece is temporarily stored (step S115), and is then sent to a subsequent process, such as an assembly process (step S116).

As described above, since the ultrasonic testing can be conducted while the air gap AG of the workpiece WK being filled up with the test liquid, the detection accuracy of the weld defect can be improved. Further, since the rotary holder jig 14 moves the workpiece WK by using the vacuum force, the components and cost of the ultrasonic testing device 10 can be reduced.

Further, since the ultrasonic testing device 10 conducts the leak test before the ultrasonic testing, the inspection efficiency can be improved. Further, since the flushing can be conducted at the time of the ultrasonic testing, the reliability of the workpiece WK can be improved.

As described above, although the present invention that is invented by the present inventor is particularly described based on the implementation and examples, the invention should not be limited to the implementation or the examples and can be changed, modified, and/or varied without departing from the scope of the invention.

Note that the present invention is not intended to be limited to the implementation or the examples described herein, and may include various modifications. For example, the implementation and the examples are to describe the invention in detail for easier understanding of the invention, and should not necessarily be limited to the configuration including all the components and elements described herein.

Further, some of the configurations of certain implementation or example may be added to, removed from, and/or replaced by some of configurations of another implementation or example.

The invention claimed is:

1. An ultrasonic testing device that immerses a differential casing to which a ring gear is welded into liquid, and detects a weld defect in a welded part of the differential casing based on an ultrasonic wave, the ultrasonic testing device comprising:
    a liquid tank that stores the liquid into which the differential casing is to be immersed;
    a workpiece holder that holds the differential casing and immerses the differential casing into the liquid in the liquid tank;
    an ultrasonic probe that conducts an ultrasonic testing of the welded part of the differential casing by irradiating the ultrasonic wave to the welded part and receiving a reflected wave;
    an image processing module that generates an ultrasonic image based on the reflected wave received by the ultrasonic probe; and
    a replacer that replaces gas inside an air gap formed at a weld toe of the welded part with test liquid,
    wherein the replacer replaces the gas inside the air gap by the test liquid before the ultrasonic probe irradiates the ultrasonic wave, and replaces the gas inside the air gap with the test liquid with the help of negative pressure generated when vacuuming the air gap.

2. The ultrasonic testing device of claim 1, wherein the replacer forces the test liquid to flow through the air gap for a predetermined period of time when replacing the gas inside the air gap with the test liquid.

3. The ultrasonic testing device of claim 1, further comprising:
    a pressure sensor that measures pressure inside the air gap; and
    a determination module that determines whether a leak due to the weld defect exists in the welded part,
    wherein the determination module monitors a pressure value measured by the pressure sensor when the replacer vacuums the air gap, and determines that a leak due to the weld defect exists in the welded part if the pressure value changes during a predetermined monitoring period of time.

4. The ultrasonic testing device of claim 1, wherein the replacer replaces the gas inside the air gap with the test liquid, via at least one air hole that releases air at the time of welding and is formed in at least either one of the differential casing and the ring gear.

5. The ultrasonic testing device of claim 1, wherein the replacer removes the test liquid inside the air gap by pressurizing the air gap after the ultrasonic testing is conducted by the ultrasonic probe.

6. The ultrasonic testing device of claim 5, wherein the replacer pressurizes the air gap via at least one air hole.

7. The ultrasonic testing device of claim 6 wherein the at least one air hole releases air at the time of welding and is formed in at least either one of the differential casing and the ring gear.

8. The ultrasonic testing device of claim 1, wherein the test liquid with which the gas inside the air gap is replaced by the replacer is the liquid stored in the liquid tank.

9. An ultrasonic testing method that tests a workpiece with an ultrasonic wave, by immersing a differential casing to which a ring gear is welded into liquid stored in a liquid tank, and detecting a weld defect in a welded part of the differential casing with the ultrasonic wave, comprising:
    immersing the differential casing into the liquid;
    replacing gas inside an air gap formed at a weld toe of the welded part with test liquid; and
    conducting the detection of the weld defect by the ultrasonic wave after the gas inside the air gap is replaced,
    wherein the replacing replaces the gas inside the air gap with the test liquid with the help of negative pressure generated when the air gap is vacuumed.

10. The ultrasonic testing method of claim 9, wherein the liquid is forced to flow through the air gap for a predetermined period of time when replacing the gas inside the air gap with the test liquid.

11. The ultrasonic testing method of claim 9, further comprising:
   monitoring a pressure value inside the air gap for a predetermined monitoring period of time when the air gap is vacuumed; and
   determining that a leak due to the weld defect exists in the welded part if the pressure value changes during the predetermined monitoring period.

12. The ultrasonic testing method of claim 9, wherein the replacing the gas inside the air gap is conducted via an at least one air hole that releases air at the time of welding and is formed in at least one of the differential casing and the ring gear.

13. The ultrasonic testing method of claim 9, further comprising removing the test liquid inside the air gap by pressurizing the air gap after the conducting the detection.

14. The ultrasonic testing method of claim 13, wherein the pressurizing the air gap is conducted via at least one air hole.

15. The ultrasonic testing method of claim 14 wherein the at least one air hole releases air at the time of welding and is formed in at least either one of the differential casing and the ring gear.

16. The ultrasonic testing method of claim 9, wherein the test liquid with which the gas inside the air gap is replaced is the liquid stored in the liquid tank.

\* \* \* \* \*